United States Patent
Johnson

(10) Patent No.: US 11,049,606 B2
(45) Date of Patent: Jun. 29, 2021

(54) DENTAL IMAGING SYSTEM UTILIZING ARTIFICIAL INTELLIGENCE

(71) Applicant: SOTA Precision Optics, Inc., Orange, CA (US)

(72) Inventor: Dustin Johnson, Fullerton, CA (US)

(73) Assignee: SOTA PRECISION OPTICS, INC., Orange, CA (US)

( * ) Notice: Subject to any disclaimer, the term of this patent is extended or adjusted under 35 U.S.C. 154(b) by 78 days.

(21) Appl. No.: 16/392,396

(22) Filed: Apr. 23, 2019

(65) Prior Publication Data

US 2019/0333627 A1    Oct. 31, 2019

Related U.S. Application Data

(60) Provisional application No. 62/662,545, filed on Apr. 25, 2018.

(51) Int. Cl.
| | |
|---|---|
| *G16H 30/40* | (2018.01) |
| *G06N 3/02* | (2006.01) |
| *A61B 6/14* | (2006.01) |
| *G06T 7/12* | (2017.01) |
| *G06T 7/00* | (2017.01) |
| *A61C 7/00* | (2006.01) |

(52) U.S. Cl.
CPC ............... *G16H 30/40* (2018.01); *A61B 6/14* (2013.01); *G06N 3/02* (2013.01); *G06T 7/0012* (2013.01); *G06T 7/12* (2017.01); *A61C 7/002* (2013.01); *G06T 2207/30036* (2013.01)

(58) Field of Classification Search
CPC ........... G06N 3/02; G06T 7/0012; G06T 7/12; G06T 2207/30036; G16H 30/40; A61B 6/14; A61C 7/002
USPC ......................................... 382/132, 156, 159
See application file for complete search history.

(56) References Cited

U.S. PATENT DOCUMENTS

| | | |
|---|---|---|
| 4,839,807 A | 6/1989 | Doi et al. |
| 4,841,555 A | 6/1989 | Doi et al. |
| 4,851,984 A | 7/1989 | Doi et al. |
| 4,875,165 A | 10/1989 | Fencil et al. |
| 4,907,156 A | 3/1990 | Doi et al. |
| 4,918,534 A | 4/1990 | Lam et al. |
| 5,072,384 A | 12/1991 | Doi et al. |
| 5,133,020 A | 7/1992 | Giger et al. |
| 5,150,292 A | 9/1992 | Hoffmann et al. |
| 5,224,177 A | 6/1993 | Doi et al. |
| 5,289,374 A | 2/1994 | Doi et al. |
| 5,319,549 A | 6/1994 | Katsuragawa et al. |
| 5,343,390 A | 8/1994 | Doi et al. |
| 5,359,513 A | 10/1994 | Kano et al. |
| 5,452,367 A | 9/1995 | Bick et al. |
| 5,463,548 A | 10/1995 | Asada et al. |

(Continued)

*Primary Examiner* — Daniel G Mariam
(74) *Attorney, Agent, or Firm* — Innovation Capital Law Group, LLP; Vic Lin

(57) ABSTRACT

A system and a method for training and utilizing deep convolutional neural networks to perform diagnostic and image enhancement operations on images of dentition uses digital images and other auxiliary parameters as inputs for a convolutional neural network. The neural network can output a tooth segmentation map, tooth identifiers, a probability map indicating the presence of caries, cavities or other dental anomalies/conditions, and recommended parameters for use in image enhancement algorithms.

12 Claims, 6 Drawing Sheets

(56) References Cited

U.S. PATENT DOCUMENTS

| | | |
|---|---|---|
| 5,491,627 A | 2/1996 | Zhang et al. |
| 5,537,485 A | 7/1996 | Nishikawa et al. |
| 5,598,481 A | 1/1997 | Nishikawa et al. |
| 5,622,171 A | 4/1997 | Asada et al. |
| 5,638,458 A | 6/1997 | Giger et al. |
| 5,657,362 A | 8/1997 | Giger et al. |
| 5,666,434 A | 9/1997 | Nishikawa et al. |
| 5,668,888 A | 9/1997 | Doi et al. |
| 5,673,332 A | 9/1997 | Nishikawa et al. |
| 5,732,697 A | 3/1998 | Zhang et al. |
| 5,740,268 A | 4/1998 | Nishikawa et al. |
| 5,742,700 A | 4/1998 | Yoon et al. |
| 5,790,690 A | 8/1998 | Doi et al. |
| 5,832,103 A | 11/1998 | Giger et al. |
| 5,873,824 A | 2/1999 | Doi et al. |
| 5,881,124 A | 3/1999 | Giger et al. |
| 5,931,780 A | 8/1999 | Giger et al. |
| 5,974,165 A | 10/1999 | Giger et al. |
| 5,982,915 A | 11/1999 | Doi et al. |
| 5,984,870 A | 11/1999 | Giger et al. |
| 5,987,345 A | 11/1999 | Engelmann et al. |
| 6,011,862 A | 1/2000 | Doi et al. |
| 6,058,322 A | 5/2000 | Nishikawa et al. |
| 6,064,716 A | 5/2000 | Siffert et al. |
| 6,067,373 A | 5/2000 | Ishida et al. |
| 6,075,878 A | 6/2000 | Yoshida et al. |
| 6,078,680 A | 6/2000 | Yoshida et al. |
| 6,088,473 A | 7/2000 | Xu et al. |
| 6,112,112 A | 8/2000 | Gilhuijs et al. |
| 6,138,045 A | 10/2000 | Kupinski et al. |
| 6,141,437 A | 10/2000 | Xu et al. |
| 6,185,320 B1 | 2/2001 | Bick et al. |
| 6,205,348 B1 | 3/2001 | Giger et al. |
| 6,240,201 B1 | 5/2001 | Xu et al. |
| 6,282,305 B1 | 8/2001 | Huo et al. |
| 6,282,307 B1 | 8/2001 | Armato et al. |
| 6,317,617 B1 | 11/2001 | Gilhuijs et al. |
| 6,819,790 B2 | 11/2004 | Suzuki et al. |
| 7,702,492 B2 | 4/2010 | Marshall |
| 7,824,346 B2 | 11/2010 | Marshall |
| 7,880,751 B2 | 2/2011 | Kuo et al. |
| 7,930,189 B2 | 4/2011 | Kuo |
| 7,970,627 B2 | 6/2011 | Kuo et al. |
| 7,987,099 B2 | 7/2011 | Kuo et al. |
| 8,126,726 B2 | 2/2012 | Matov et al. |
| 8,417,010 B1 | 4/2013 | Colby |
| 8,768,036 B2 | 7/2014 | Caligor et al. |
| 8,848,991 B2 | 9/2014 | Tjioe et al. |
| 9,439,610 B2 | 9/2016 | Chen et al. |
| 2017/0185871 A1* | 6/2017 | Zhang .................. G06N 3/084 |
| 2018/0039733 A1* | 2/2018 | Golay ..................... A61B 6/14 |
| 2019/0180443 A1* | 6/2019 | Xue ........................ G06K 9/66 |
| 2019/0313963 A1* | 10/2019 | Hillen ................. G06N 3/0454 |

* cited by examiner

DENTAL IMAGING SYSTEM UTILIZING ARTIFICIAL INTELLIGENCE

CROSS-REFERENCE TO RELATED APPLICATIONS

This application claims the benefit of priority of U.S. provisional patent application No. 62/662,545, filed Apr. 25, 2018, the contents of which are herein incorporated by reference.

FIELD OF THE INVENTION

Embodiments of the disclosure relate to the field of intraoral and extraoral imaging systems for use in the dental field. One specific embodiment of the disclosure relates to the utilization of artificial intelligence and machine learning in dental imaging systems for computer-aided detection of dental abnormalities and the application of image enhancements.

BACKGROUND OF THE INVENTION

Artificial intelligence has driven enormous growth in industries ranging from the hard sciences to marketing to social media, but research, development, and adoption of such technologies in the dental space has lagged significantly. Most dental offices around the world continue to use imaging software dating from the early 2000's because the field of software in the dental space has remained stagnant.

Dental imaging software is used to interface with hardware devices such as intraoral cameras, intraoral X-ray sensors, scanners, panoramic X-ray machines, cephalometric X-ray machines, Cone Beam Computed Tomography (CBCT) machines, and more, for obtaining, enhancing, storing, and managing images of patient dentition. Most imaging software products offer some capabilities for the user to apply contrast, gamma, sharpness, and other filters to acquired images to enhance image quality, aiding in the diagnosis of abnormalities in patient dentition and monitoring of treatment. The settings for these filters are typically customized only during the initial installation of the software and then applied to all images taken thereafter, and thus are not ideal for any image or even for a particular set of images.

Problems with patient dentition (such as caries, cavities, and other abnormalities and conditions) are detected manually using relatively subjective criteria by personnel who are trained to diagnose and treat such problems. Images are typically labeled for the teeth that they contain using a standardized number system. Dental office staff either select the teeth present in an image after image acquisition, or more commonly, follow a standard template or image layout series that may not apply in all cases to all patients. In cases where a layout may not contain the correct teeth number labels for each image, it can be time consuming for dental office staff to edit the labels, and because it is done manually there is room for error which can potentially lead to misdiagnosis or misidentification of an afflicted tooth.

After images are acquired and patient ailments related to their dentition have been diagnosed, treatment is scheduled. Procedures for diagnosis and treatment are typically assigned a code by the American Dental Association (ADA). For example, D2330 is the ADA code for a direct resin-based composite restoration on one surface of an anterior tooth. When dental services are rendered (or about to be rendered), dental office staff must manually query an insurance database to ensure the patient will be covered, then update their patient insurance filings and keep track of the treatment they have provided. Some of this process is managed by other software (e.g. practice management software), but generally this record keeping process requires manual entry.

Conventional methods for automated diagnosis of caries and other dental conditions utilize a heuristic/algorithmic approach that is applied to determine the contours of teeth and perform segmentation prior to anomaly detection and classification. In some conventional methods, the probability and extent of the decay of bone density is calculated exclusively through heuristic methods.

In some conventional methods, several heuristic algorithms are applied to an image in question (including an image segmentation heuristic) prior to passing image data and derived parameters to a neural network. Before image classification/diagnostics can begin, dentist feedback is required to approve the segmented image or re-process the image segmentation with user feedback, followed by more traditional heuristic-based enhancements and parameter calculations. Only after parameters and other information is gained through heuristics can those results be fed into a neural network utilizing backpropagation.

SUMMARY OF THE INVENTION

According to embodiments of the present invention, no heuristic computations or calculations are required prior to the image being fed into a convolutional neural network. Image feature recognition and segmentation is integrated into the neural network itself for tooth identification, and anomaly detection and diagnosis can be performed by the deep neural network without segmentation being applied or determination of any parameters or image features via heuristic methods. This is highly beneficial as the system can be made more flexible in its scope of application. Heuristic algorithms for feature detection are capable of only detecting a specific feature or class of features. Heuristic algorithms need to be re-written or updated to reflect changes in the features they are designed to detect. The present invention, utilizing a model trained with a convolutional neural network, is capable of continuously adapting to the data it receives as input with limited human intervention. It does not rely on heuristic methods.

BRIEF DESCRIPTION OF THE DRAWINGS

Embodiments of the invention are illustrated by way of example and not by way of limitation in the figures of the accompanying drawings, in which like references indicate similar elements and in which:

FIG. 5A illustrates a typical bitewing dental X-Ray image acquired with an intraoral X-Ray sensor and where the gray masked regions in FIG. 5B indicate pixels belonging to subregions identified by a neural network to belong to a tooth structure;

DETAILED DESCRIPTION

Figure 1:
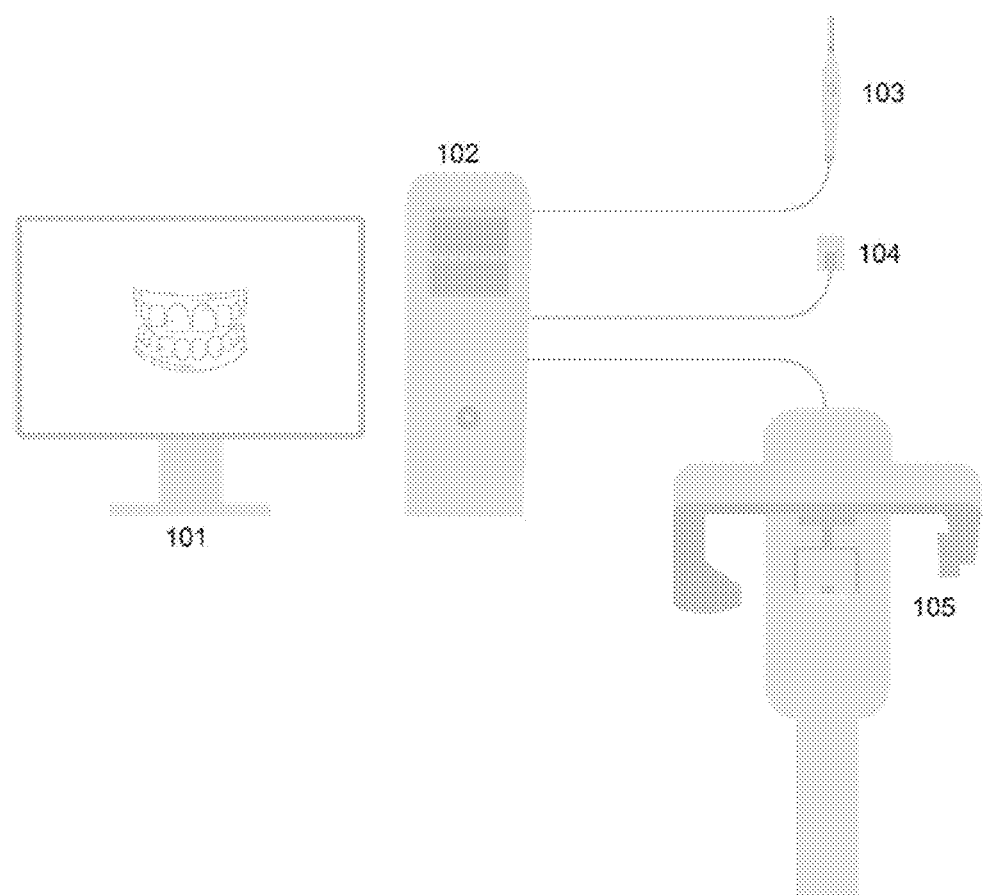
FIG. 1 illustrates components of a digital imaging system using wired transmission mediums, including a computer (102), a monitor (101), an intraoral camera (103), an intraoral X-Ray sensor (104), and a panoramic X-Ray machine (105)

Embodiments of an apparatus, a system, and a method for automated dental image manipulation, enhancement, labeling, tagging, and recognition of abnormalities in dentition are described. The dental imaging system provided utilizes models trained via methods of machine learning (specifically deep learning utilizing synthetic neural networks) to aid in the performance of tasks that are typically done manually by dental office staff. This apparatus/system/method can be deployed to both cloud webservices and individual devices, and methods for training the models. The invention can be used with any dental imaging implement. Some examples of implements used for dental imaging include intraoral cameras, digital intraoral X-ray sensors, panoramic X-ray machines, and cephalometric X-ray machines.

One embodiment of the dental imaging system can recognize the orientation of the X-ray sensor/intraoral camera and rotate the image according to the arrangement of the teeth present in the image and sensor geometry. A typical embodiment uses a convolutional neural network to train a model. Such a model can be trained using a statistically significant sample of images that have been pre-labeled/numbered according to the teeth present in the image and optionally the orientation of the sensor or camera that took the image. The model can optionally use accelerometer or gyroscope data provided by hardware in the intraoral X-ray sensor/intraoral camera or sensor holders/bite-blocks/collimators that were used to acquire the image for increasing accuracy in tooth number determination and orientation. The model used for such an embodiment can be improved over time by continuously integrating newly acquired images from multiple devices, office locations, and dental office staff into its existing training set through the use of, for example, a cloud-based imaging software integration. This embodiment improves on previous inventions by not requiring implement specific sensors or markers to be present in the imaging implement used to acquire an image, nor does it require manufacturer specific code or software to determine the implement orientation. This is advantageous because it can be applied universally to images acquired by any implement belonging to a particular class of imaging device (i.e. intraoral sensors, panoramic x-ray machines).

One embodiment of the dental imaging system can automatically determine what teeth are present in an intraoral X-Ray or camera image. A typical embodiment uses a convolutional neural network to train a model. Such a model can be trained using a statistically significant sample of images that have been pre-labeled/numbered according to the teeth present in the image. The model can optionally use accelerometer or gyroscope data provided by hardware in the intraoral sensor/camera or sensor holders/bite-blocks that were used to acquire the image for increasing accuracy in tooth position recognition. The output of this embodiment is both a probability map indicating the likelihood of a pixel or sub-region of pixels belonging to the target structure (teeth), as well as locations for the teeth, via a standard method of object localization or segmentation utilized in machine vision (i.e. a Mask R-CNN/Bayesian Optimization/Semantic Segmentation). The model used for such an embodiment can be improved over time by continuously integrating newly acquired images from multiple devices, office locations, and dental office staff into its existing training set through the use of, for example, a cloud-based imaging software integration. Such an embodiment improves the process of labeling teeth in an image, by helping to prevent accidental mislabeling by office staff, saving office staff valuable time, and cutting down the amount of time patients spend waiting for office staff to do routine annotation of images. Additionally, this embodiment improves on existing dental imaging software by breaking the industry paradigm of requiring office staff to acquire images in a particular order that has been pre-set by a user or the manufacturer in a template, allowing each member of dental office staff to take images in the order they prefer.

One embodiment of the dental imaging system can analyze the acquired image and adjust contrast, sharpness, gamma, gain, and other image characteristics. A typical embodiment uses a convolutional neural network to train a model. Such a model can be trained using a statistically significant sample of images that have been pre-labeled with values of their contrast, sharpness, gamma, gain, and other image characteristics, in addition to a "quality score" that rates the image quality. Since such an adjustment may be subjective or particular to a specific field of dentistry or specific problems related to the dentition in question, each X-ray image in the sample image set can be quantitatively rated for quality according to different sets of standards determined by experts in their particular field (i.e. endodontics, periodontics, orthodontics). The model used for such an embodiment can be improved over time by continuously integrating newly acquired images from multiple devices, office locations, and dental office staff into its existing training set through the use of, for example, a cloud-based imaging software integration or SaaS. This embodiment of the invention improves on previous dental imaging software by dynamically improving the parameters involved in image enhancement on a per-image basis, so that each enhancement is tailored to the particular image in question rather than reliant on the quality of a single initial configuration.

One embodiment of the dental imaging system can analyze an acquired image and automatically detect and highlight/indicate the presence of abnormalities in dentition (for example but not limited to caries and cavities). A typical embodiment uses a convolutional neural network to train a model. Such a model can be trained using a statistically significant sample of images that have been pre-labeled by dental experts as having or not having particular abnormalities/afflictions in the dentition. The output of this embodiment is both a probability map indicating the likelihood of a pixel or sub-region of pixels belonging to the target structure (teeth), as well as locations for the teeth, which can be achieved via a method of object localization or segmentation in machine vision using deep learning (i.e. an R-CNN/Bayesian Optimization/Semantic Segmentation). Labels for abnormalities/afflictions can be attached or annotated on the images reflecting the ADA standard nomenclature and automate portions of the treatment planning and insurance filing process based on the detected affliction. The model used for such an embodiment can be improved over time by continuously integrating newly acquired images from multiple devices, office locations, and dental office staff into its existing training set using, for example, a cloud-based imaging software integration. This embodiment of the invention improves on existing dental imaging software by providing dental staff with an instant second opinion on the condition of the dentition present in the images, and potentially saves time by automating and assisting with the labeling and documentation of anomalies present in the images and filed in insurance claims.

I. TERMINOLOGY

In the following description, certain terminology is used to describe features of the invention. In certain situations, the term "logic" is representative of hardware, firmware, and/or software that is configured to perform one or more functions. As hardware, the logic may include circuitry having data processing or storage functionality. Examples of such circuitry may include, but are not limited or restricted to a microprocessor, one or more processor cores, a programmable gate array, a microcontroller, an application specific integrated circuit, wireless receiver, transmitter and/or transceiver circuitry, semiconductor memory, or combinatorial logic.

Alternatively, or in combination with the hardware circuitry described above, the logic may be software in the form of one or more software modules. The software module(s) may include an executable application, an application programming interface (API), a subroutine, a function, a procedure, an applet, a servlet, a routine, source code, a shared library/dynamic load library, or one or more instructions. The software module(s) may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; a semiconductor memory; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the executable code may be stored in persistent storage.

The term "computerized" generally represents that any corresponding operations are conducted by hardware in combination with software and/or firmware.

The term "automated" generally represents that any corresponding operations are conducted by hardware in combination with software and/or firmware.

The term "network device" may be construed as a physical, electronic device that is based on the execution of one or more software modules. The network device may be communicatively coupled to a public network such as the Internet or a private network such as a wireless data telecommunication network, wide area network, a type of local area network (LAN), or a combination of networks. Examples of the network device may include, but are not limited or restricted to physical electronic devices such as a personal computer such as a desktop, laptop, tablet or netbook; a mobile phone; a standalone appliance; a sensor; an intraoral imaging wand, etc.

The term "transmission medium" may be construed as a physical or logical communication path between two or more electronic devices. For instance, as a physical communication path, wired and/or wireless interconnects in the form of electrical wiring, optical fiber, cable, bus trace, or a wireless channel using infrared, radio frequency (RF), may be used.

The term "machine learning" refers to a subfield of computer science that focuses on the development of computer programs capable of accessing and using data to learn for themselves, without being explicitly programmed to do so.

The term "deep learning" refers to a subset of machine learning that involves networks which are capable of learning based on data representations, rather than task-specific algorithms. "Deep learning" can be supervised, semi-supervised, or unsupervised. Deep learning models are loosely related to information processing and communication patterns in a biological nervous system, such as neural coding that attempts to define a relationship between various stimuli and associated neural responses in the brain.

The term "neural network" refers to a computer system modeled on the human brain and nervous system.

The term "feed forward neural network" refers to an artificial neural network wherein connections between the units do not form a cycle. They typically include an input layer, one or more hidden layers, and an output layer.

The term "convolutional neural network" (abbr. CNN) refers to a class of deep, feed-forward artificial neural networks that can be used to analyze visual imagery and include at least one convolutional layer.

The term "activation function" refers to a function that is an abstraction representing the firing of a neuron in a biologically inspired neural network.

The term "Mask R-CNN" (mask regional convolutional neural network) refers to a method in the field of machine vision to perform pixel-based image segmentation. Mask R-CNNs can perform both image segmentation and classification.

The term "sigmoid function" refers to a mathematical function having a characteristic "S"-shaped curve (known as a sigmoid curve). A wide variety of sigmoid functions are used in applications of artificial intelligence and machine learning as the activation functions of artificial neurons.

The term "semantic segmentation" refers to a process used in the field of machine vision for the purpose of dividing an image into semantically meaningful parts, and to classify those parts as being a member of a pre-defined category.

The term "rectified linear unit" (commonly abbreviated ReLU) refers to a type of rectifier used as an activation function for deep neural networks.

The term "backpropagation" is short for "backwards propagation of errors." Backpropagation is a method used in artificial neural networks to calculate a gradient that is needed in the calculation of weights to be used in the network.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

TRAINING

Models may be trained using the process of backpropagation or another form of automatic differentiation. Training data may include, for example, pre-labeled or pre-classified images from traditional imaging software, electronic health records, converted paper records, or data gathered using a software-as-a-service or cloud platform. Pre-processing of image data may vary widely depending on the exact implementation or embodiment of the invention and the input data, but can include, for example, the resizing of images to some standardized dimensions, the interpretation of positional indicators of sensors into some standardized form, conversion of images to a standardized "bit-ness" or color depth, cropping images or otherwise modifying their aspect ratio to a standardized value, the normalization of image pixel values, reducing the dimensionality of colored (non-grayscale) images, or perturbation of the training data to augment the size and robustness of the training data set.

GENERAL ARCHITECTURE

The neural network can be deployed as a software package for integration into a standalone PC application, a local server, or to a remote server for offsite processing.

Figure 2:
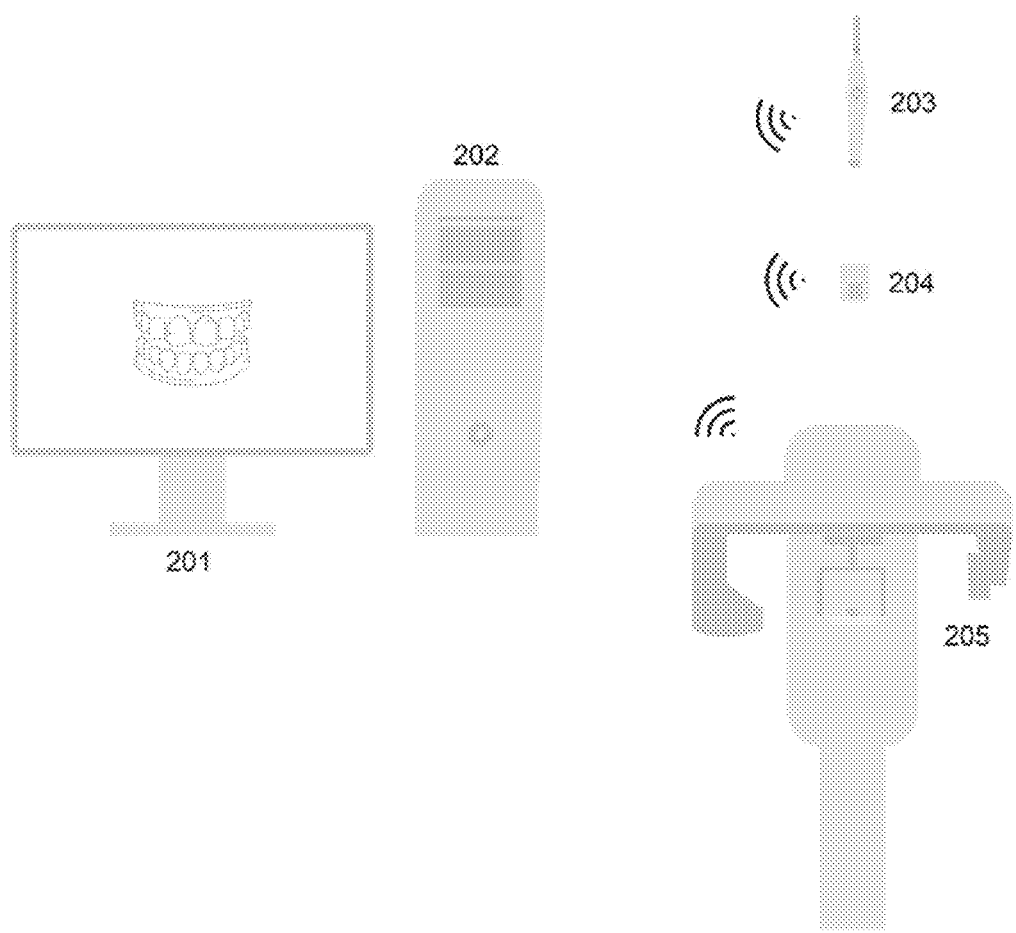
FIG. 2 illustrates components of a digital imaging system using wireless transmission mediums, including a computer (202), a monitor (201), an intraoral camera (203), an intraoral X-Ray sensor (204), and a panoramic X-Ray machine (205)

Dental imaging devices are typically connected to a computer during acquisition or use an embedded system to transfer images to a receiving system. Receiving systems can include a PC, a local server, or a remote server. Images acquired by the device are sent to the receiving system either by a direct, wired connection (FIG. 1) or as a radio signal or wireless network connection (FIG. 2).

Figure 3:
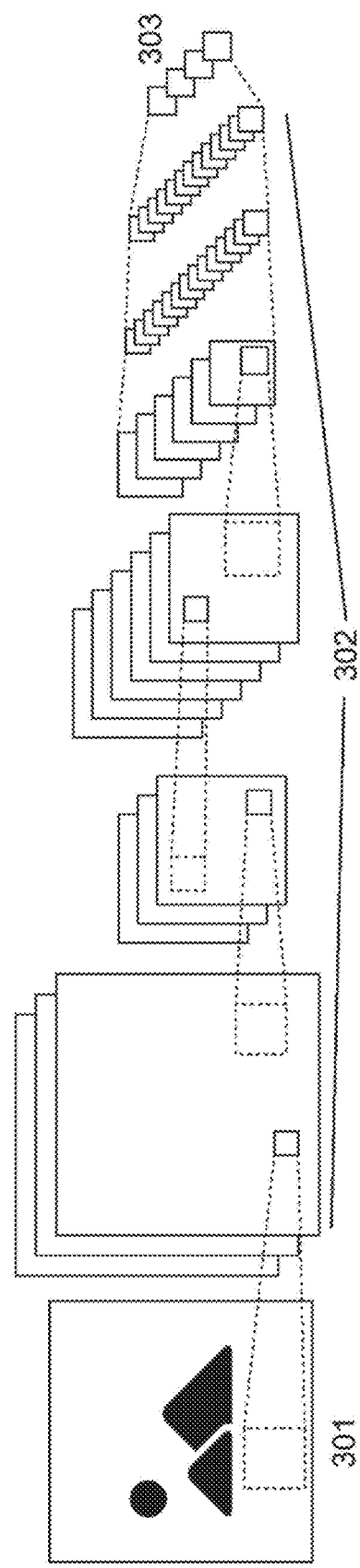
FIG. 3 illustrates a generic deep convolutional neural network including an input layer (301), a hidden layer (302), and an output layer (303)
Figure 4:
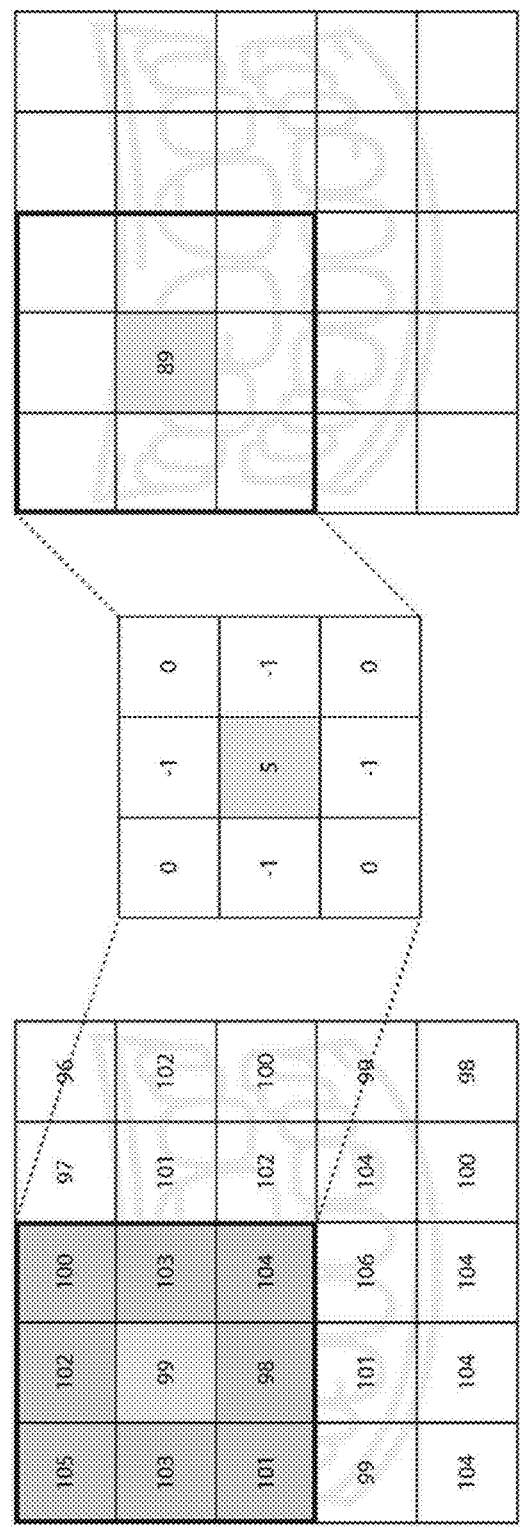
FIG. 4 illustrates the application of a generic convolution kernel to image data.
Figure 5A:
FIGS. 5A and 5B are illustrations of a probability map indicating the likelihood of each individual pixel in an image corresponding to a structure that the neural network is intended to identify or locate (in this case, teeth), where
Figure 5B:
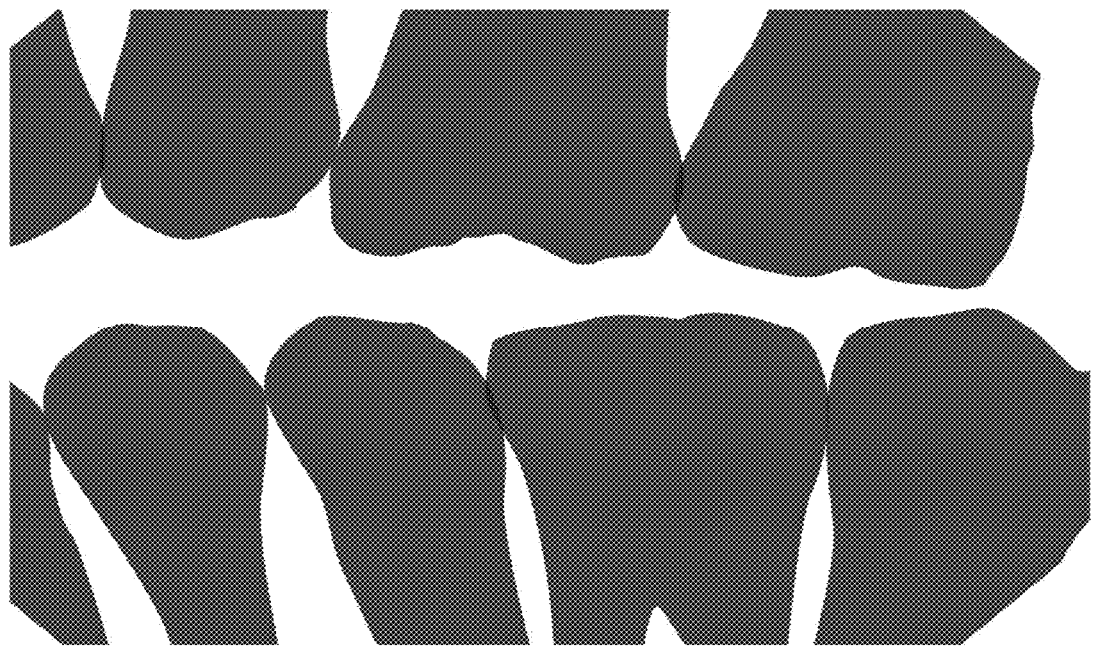
Figure 6:
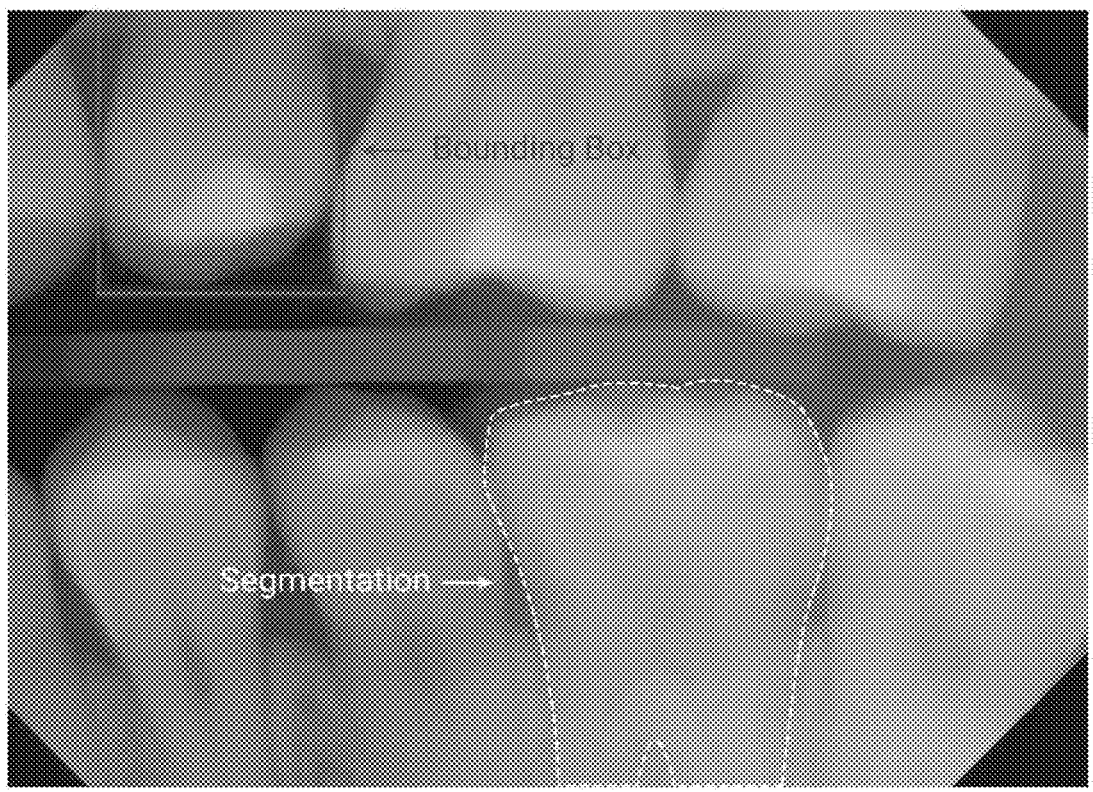
FIG. 6 illustrates the concept of a bounding box and feature segmentation applied to an intra-oral X-Ray image.

Upon image acquisition and delivery to the receiving system, the imaging software begins processing the image through one or more convolutional neural networks (FIG. 3), depending on the embodiment of the invention. In a typical embodiment the image is processed through up to four neural networks either in parallel or in series. Each neural network may include one or more input layers (301), one or more hidden layers (302), and one or more output layers (303). In this example, each component of each input layer would correspond to one or more features of the input data set (i.e. the image data, the position readout from an embedded gyroscope or accelerometer in the imaging device or from a marking pixel at a predetermined location on the image sensor, the device model, etcetera). Each hidden layer may include multiple components that each learn a distinct set of weights representing the values of functions applied to the input data (components of a hidden layer may include convolution units (FIG. 4), sigmoid functions, rectified linear units, pooling units, subsampling units, segmentation units, and classification units including fully connected layers). In a typical configuration, the output of the neural network can indicate the probability of an image having been acquired with the imaging device in a certain orientation or at a certain location in the mouth, or the probability that the image contains certain teeth and the locations of those teeth, or probabilities corresponding to the ideal parameters to apply to image enhancement filters/algorithms, or the probability of an image or section of tooth containing caries/cavities, or any combination of those probabilities, depending on user selection or system configuration.

Images may subsequently be tagged in practice management or other claims handling software using a standardized treatment code (i.e. an ADA treatment code).

In the foregoing description, the invention is described with reference to specific exemplary embodiments thereof. However, it will be evident that various modifications and changes may be made thereto without departing from the broader spirit and scope of the invention as set forth in the appended claims.

What is claimed is:

1. A computer-implemented method of training an artificial neural network for automatic dental image manipulation, enhancement, labeling, tagging, and recognition of abnormalities in dentition, caries and/or cavities, the method comprising:
    receiving at least one set of training images and their associated labels, wherein the at least one set of training images includes images containing teeth and is representative of only one category of imaging implement;
    passing the set of training images and the associated labels to an artificial neural network; and
    using a technique of backpropagation to determine statistical weights corresponding to a likelihood that values of each pixel or a pooled sub-region of pixels in an input image collectively represent a structure or state that a neural network model is intended to identify, wherein
    image feature recognition and segmentation is integrated into the artificial neural network itself for tooth identification, and anomaly detection and diagnosis is performed by the artificial neural network without segmentation being applied or determination of any parameters or image features via heuristic methods.

2. The method of claim 1, wherein:
    the target artificial neural network that is passed the training data set utilizes one or more of the following: one or more convolution layers, one or more rectified linear units (ReLUs), one or more pooling layers, one or more fully connected layers, and includes at least one input layer, one hidden layer, and one output layer.

3. The method of claim 2, wherein:
    the at least one set of training images includes images that have been labeled according to one or a combination of the following: an image orientation, the teeth contained within the image, parameters associated with image enhancements that have been applied to the image, what anomalies in the dentition are present.

4. The method of claim 3, wherein:
    the at least one set of training images includes images that have been labeled with pixel coordinates of rectangles containing locations of the teeth.

5. The method of claim 3, wherein the at least one set of training images includes images that have been labeled with a segmentation map corresponding to locations of the teeth.

6. The method of claim 3, wherein:
    the step of receiving at least one set of training images is representative of one or more of the following scenarios:
    i) the at least one set of training images includes images oriented in such a way that each possible multiple of 90° rotations are represented, with labels indicating an amount of rotation for each image;
    ii) the at least one set of training images includes images representative of each tooth typically present in the dentition of both anatomically normal and abnormal adults and/or children, with labels indicating what teeth are present in each image;
    iii) the at least one set of training images includes images representing a statistically significant portion of an image enhancement parameter space with labels indicating enhancement parameters and a qualitative rating of those parameters;

iv) the at least one set of training images includes images representing dental anomalies and/or dental conditions, in addition to healthy dentition, with labels indicating the presence of an anomaly and/or a dental condition, or a plurality of anomalies and/or dental conditions; and v) images in the at least one set of training images have been perturbed or manipulated to augment the size of the training set to the benefit of the resulting model.

7. The method of claim 3, wherein:

the one or more convolution layers of the target artificial neural network can apply convolution to one or more of: consecutively overlapping sub-regions of each image in the at least one set of training images, or to consecutive, non-overlapping sub-regions of each image in the at least one set of training images, or to non-consecutive overlapping or non-overlapping sub-regions of each image in the at least one set of training images.

8. A computer system having non-transitory computer readable media with imaging software embedded therein, the imaging software including code which when executed on a processor of the system causes the system to implement the artificial neural network trained by the method of claim 1.

9. The artificial neural network of claim 8 wherein:

the artificial neural network includes parameters that dictate an operation and behavior of the network, which are trained to minimize error during the process of backpropagation; and the neural network outputs a probability map indicating a per-pixel or per-sub-region likelihood of each pixel or sub-region being part of a structure or state that the neural network is intended to locate and/or identify.

10. The artificial neural network of claim 9 wherein:

the neural network outputs a bounding box or segmentation map derived from the per-pixel or per-sub-region likelihood of each pixel or sub-region being part of the structure or state that the neural network is intended to locate and/or identify.

11. The artificial neural network of claim 9, wherein:

the neural network outputs labels or tags corresponding to the state or structure that the neural network is intended to locate and/or identify.

12. The artificial neural network of claim 9, wherein:

the neural network outputs one or more image filter parameters optimized for an input image and representative of contrast, gamma, sharpness, and/or other related enhancements.

\* \* \* \* \*